(12) United States Patent
O'Brien

(10) Patent No.: US 7,008,438 B2
(45) Date of Patent: Mar. 7, 2006

(54) ANCHORED PTCA BALLOON

(75) Inventor: Dennis O'Brien, Oceanside, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 6 days.

(21) Appl. No.: 10/618,987

(22) Filed: Jul. 14, 2003

(65) Prior Publication Data

US 2005/0015107 A1    Jan. 20, 2005

(51) Int. Cl.
*A61B 17/22* (2006.01)
(52) U.S. Cl. .................. 606/159; 606/194; 606/103.08
(58) Field of Classification Search ............... 623/1.11, 623/1.23, 1.36, 1.28; 606/191–200, 159; 604/103.01–103.08, 104, 106, 109, 101.02, 604/507–509
See application file for complete search history.

(56) References Cited

U.S. PATENT DOCUMENTS

| | | | |
|---|---|---|---|
| 3,746,003 A | 7/1973 | Blake et al. | |
| 3,833,004 A | 9/1974 | Vazquez et al. | |
| 3,995,623 A | 12/1976 | Blake et al. | |
| 5,009,659 A | 4/1991 | Hamlin et al. | |
| 5,112,305 A | 5/1992 | Barath et al. | |
| 5,242,397 A | 9/1993 | Barath et al. | |
| 5,308,325 A | 5/1994 | Quinn et al. | |
| 5,329,942 A | 7/1994 | Gunther et al. | |
| 5,395,331 A * | 3/1995 | O'Neill et al. ......... | 604/103.08 |
| 5,423,745 A | 6/1995 | Todd et al. | |
| 5,439,444 A | 8/1995 | Andersen et al. | |
| 5,484,412 A | 1/1996 | Pierpont | |
| 5,487,730 A | 1/1996 | Marcadis et al. | |
| 5,527,292 A | 6/1996 | Adams et al. | |
| 5,569,195 A | 10/1996 | Saab | |
| 5,599,306 A | 2/1997 | Klein et al. | |
| 5,620,418 A | 4/1997 | O'Neill et al. | |
| 5,704,913 A * | 1/1998 | Abele et al. ............ | 604/101.02 |
| 5,807,326 A | 9/1998 | O'Neill et al. | |
| 6,562,062 B1 | 5/2003 | Jenusaitis et al. | |
| 2001/0001812 A1 | 5/2001 | Valley et al. | |
| 2003/0032973 A1 | 2/2003 | Jenusaitis et al. | |

FOREIGN PATENT DOCUMENTS

| | | |
|---|---|---|
| EP | 0359489 A2 | 3/1990 |
| WO | WO 01/97895 A2 | 12/2001 |

* cited by examiner

*Primary Examiner*—Anhtuan T. Nguyen
*Assistant Examiner*—Elizabeth Houston
(74) *Attorney, Agent, or Firm*—Nydegger & Associates

(57) ABSTRACT

A catheter is provided having a system for anchoring an inflatable balloon at a treatment site. The system includes a flexible member having a substantially cylindrical shaped wall that defines a longitudinal axis. The outer surface of the cylindrical wall is formed with a plurality of protuberances that each project radially outward from the wall. With this structure, the wall seamlessly interconnects the protuberances together. In one embodiment, the flexible member constitutes a portion of a dilatation balloon. In another embodiment, the flexible member is formed as a jacket that is placed over and bonded to a dilatation balloon. The protuberances are sized, shaped and spaced on the wall of the flexible member to allow each protuberance to penetrate and become embedded in a lesion at a treatment site during inflation of the balloon. Once embedded, the protuberances anchor the balloon at the treatment site.

16 Claims, 3 Drawing Sheets

ANCHORED PTCA BALLOON

FIELD OF THE INVENTION

The present invention pertains generally to devices that are used for performing medical procedures. More particularly, the present invention pertains to medical devices that can be inflated or expanded in the vasculature of a patient. The present invention is particularly, but not exclusively, useful as a system and method for anchoring a medical device to a lesion in a vessel of a patient after the device has been inflated or expanded.

BACKGROUND OF THE INVENTION

Many interventional medical procedures require that a medical device be inserted into the vasculature of a patient to perform a surgical operation on the patient. Often, it is necessary that such devices be reconfigured once they have been positioned in the vasculature. For instance, many medical procedures require the use of a device that can be inflated or expanded. Typically, in these cases, the device is attached to the distal end of a catheter, which is advanced through the vasculature to position the device at a lesion in a vessel of the patient. The device is then expanded or inflated at the lesion during the surgical operation. For example, the device could be a balloon or some other such device that is inflated to dilate a lesion in a vessel of the patient.

One common interventional medical procedure, which uses a balloon catheter, is percutaneous transluminal coronary angioplasty (PTCA). In a typical PTCA procedure, a dilatation balloon of the balloon catheter is advanced through the vasculature of a patient with the balloon in a deflated configuration. The balloon is then precisely positioned next to a lesion in the vessel that is to be treated. Once the balloon has been properly positioned, fluid is infused into the balloon to expand the balloon into an inflated configuration. As the balloon expands, it presses against the lesion and dilates the lesion to increase the effective diameter of the vessel. In turn, the portion of the lesion that is in contact with the balloon produces reactive forces on the balloon. For a lesion that is lubricious, the reactive forces may overcome the frictional forces between the balloon and the lesion. If this happens, slippage occurs between the balloon and the lesion, and results in unwanted movement of the balloon relative to the lesion. For instance, the reactive forces can cause the balloon to shoot forward or backward through the vessel in a longitudinal direction (i.e., "the watermelon seed effect"). This unwanted movement is to be avoided because the dilatation procedure does not occur precisely at the desired location in the vessel and, thus, the effectiveness of the PTCA procedure is reduced.

Various devices and methods have been suggested for preventing the unwanted longitudinal movement of a medical device as it is being expanded or inflated in the vasculature of a patient. For example, U.S. Pat. No. 5,620,418, which issued to O'Neill et al. for an invention entitled "Retrograde Coronary Sinus Catheter," incorporates segmented, annular ribs on a balloon device for frictionally engaging the coronary sinus of the heart. The device disclosed in the O'Neill et al. reference, however, relies on a frictional component between the ribs and the coronary sinus to prevent unwanted movement of the device without penetrating the ribs into the walls of the coronary sinus. Other suggested devices for preventing unwanted movement of a medical device as it is being expanded or inflated in the vasculature incorporate structures for penetrating a lesion in a vessel of the patient. Typically, these structures are mounted on the outer surface of an inflatable balloon to penetrate the lesion as the balloon is being inflated. For example, U.S. patent application Ser. No. 09/927,135, which was filed by Jenusaitis et al. for an invention entitled "Balloon Anchoring System" and which is assigned to the same assignee as the present invention, incorporates stainless steel cutting blades with azimuthal segments that are mounted on the surface of a balloon. As the balloon expands in a vessel, the cutting blades and the azimuthal segments penetrate a lesion in the vessel to anchor the balloon to the lesion and thereby prevent unwanted movement of the balloon in the vessel. For these types of devices, however, the cutting blades and the balloon are separate structures that are typically made from different materials and that must somehow be joined together during manufacture. Typically, this manufacturing process is labor intensive and costly.

In light of the above, it is an object of the present invention to provide a system and method for preventing unwanted movement of a medical device while the device is being expanded or inflated in a vessel of a patient. Another object of the present invention is to provide a balloon with protuberances on the outer surface thereof for penetrating a lesion in a vessel of a patient, wherein the balloon and the protuberances are made of the same material. Still another object of the present invention is to provide a balloon that has protuberances seamlessly and integrally interconnected with the outer surface of the balloon for penetrating the protuberances into a lesion in a vessel of a patient to anchor the balloon to the lesion. Yet another object of the present invention is to provide a system for anchoring a medical device to a lesion in the vasculature of a patient that is relatively simple to manufacture, easy to use, and comparatively cost effective.

SUMMARY OF THE INVENTION

In accordance with the present invention, a medical device is provided which includes a flexible member having a substantially cylindrical shaped wall that defines a longitudinal axis. The outer surface of the cylindrical wall is formed with a plurality of protuberances that project outwardly from the wall. With this cooperation of structure, the wall seamlessly interconnects each protuberance with the remaining protuberances. In one embodiment of the present invention, the flexible member constitutes the working portion of a dilatation balloon. More specifically, in this embodiment the flexible member is formed integrally with a pair of enclosures to establish the dilatation balloon. In another embodiment, the flexible member is formed as a jacket that is placed over and bonded to the working portion of a dilatation balloon.

In greater structural detail, the protuberances are sized, shaped and spaced on the outer surface of the flexible member to allow each protuberance to penetrate and become embedded in a lesion at a treatment site during inflation of the balloon. Once embedded, the protuberances anchor the balloon at the treatment site. In one embodiment, the protuberances are formed as a plurality of cleats having sufficient cleat length and inter-cleat spacing to allow one or more cleats to embed in the lesion during balloon inflation. In another embodiment, the protuberances are formed as a plurality of raised ridges with each ridge extending radially from the cylindrical wall of the flexible member to a relatively sharp edge that is aligned substantially parallel to the longitudinal axis.

In a first method for manufacturing the device, a polymeric material, such as polyethylene terephthalate (PET), is heated to a working temperature and extruded through a die. More specifically, the die is configured to produce an extrusion having a plurality of longitudinally aligned ridges that extend radially outward from the outer surface of a cylindrically shaped wall. Next, the extrusion is radially expanded to form a balloon using, for example, a free-blow or blow-mold process. The result is a balloon having a plurality of longitudinally aligned ridges that extend radially outward from the outer surface of the balloon. In some cases, portions of each ridge are selectively removed (i.e., trimmed) from the outer surface of the balloon to establish protuberances having a desired shape and arrangement. Alternatively, selected portions of each ridge can be removed from the extrusion. The trimmed extrusion is then expanded to create a balloon with protuberances having a desired shape and arrangement.

In another method for manufacturing the device, a tube made of a polymeric material and having a substantially cylindrical-shaped outer surface is placed in the cavity of a mold. For this method, the mold is formed with a substantially cylindrical-shaped mold surface having a plurality of recesses. Each recess is shaped to conform with the desired shape of a protuberance. Once inside the mold cavity, the tube is radially expanded to form a balloon having protuberances with a desired shape and arrangement on the outer surface of the balloon.

In another method for manufacturing the device, a one-piece, flexible member which is typically a flexible sheet or a flexible tube, is formed having a plurality of protuberances on its outer surface. In this method, the flexible member is typically made of a polymeric material and formed in either an extrusion or injection molding process. The inner surface of the flexible member (i.e., the surface opposed to the outer surface with the protuberances) is bonded to the cylindrical outer surface of a dilatation balloon. For example, the flexible member can be adhesively, thermally or ultrasonically bonded to the balloon.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
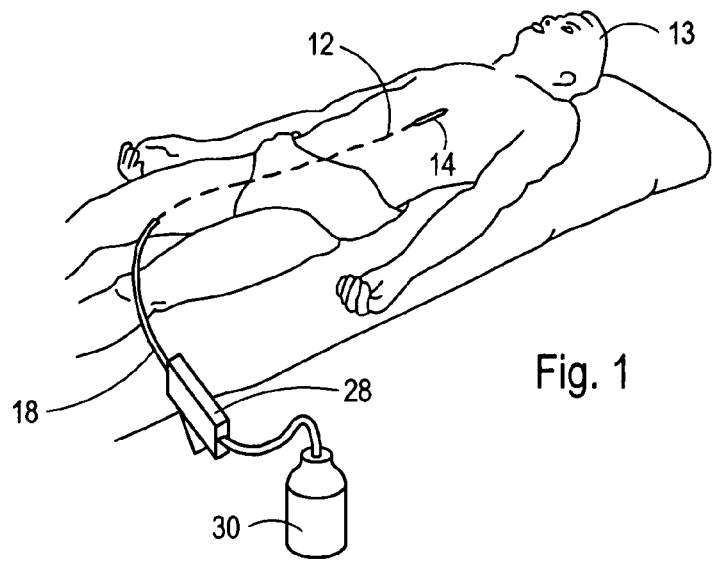
FIG. 1 is a simplified, perspective view of a catheter having a balloon and a system for anchoring the balloon at an internal treatment site, showing the catheter operationally positioned in the upper body of a patient.

Referring initially to FIG. 1, a catheter 12 is shown for performing a medical procedure at an internal treatment site of a patient 13. More specifically, the catheter 12 is shown positioned to treat a lesion in an upper body artery. Although the catheter 12 is capable of performing a medical procedure in an upper body artery such as a coronary artery, those skilled in the pertinent art will recognize that the use of the catheter 12 as herein described is not limited to use in a specific artery, but, instead can be used in vascular conduits and other ductal systems throughout the human body.

Figure 2:
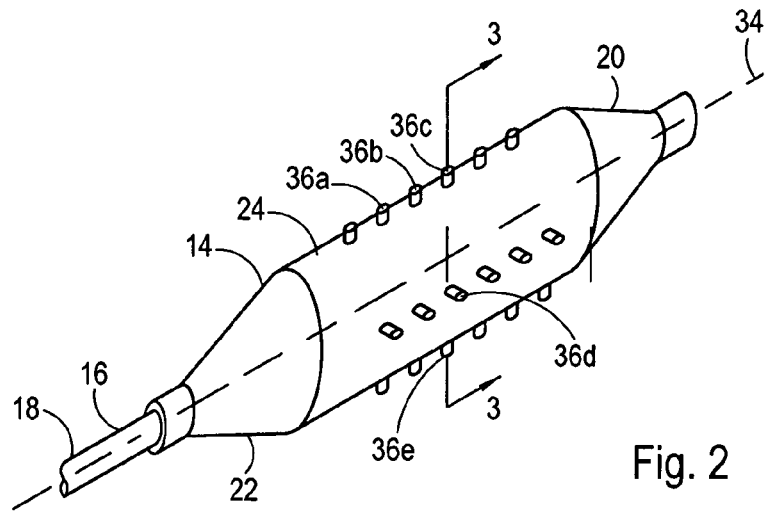
FIG. 2 is an enlarged, perspective view of the distal end of the catheter shown in FIG. 1, showing the balloon after balloon inflation.

Referring now to FIG. 2, the distal portion of the catheter 12 is shown to include an inflatable dilatation balloon 14 that is attached to the distal end 16 of an inflation tube 18. As best seen in FIG. 2, the one-piece balloon 14 can be characterized as having three sections; a distal enclosure 20, a proximal enclosure 22 and a flexible member 24. In combination, the enclosures 20, 22, which, as shown, typically have a somewhat conical shape, and the flexible member 24 cooperate to surround an inflation volume 26 (see FIG. 3) that can be infused with a medical grade fluid to inflate the balloon 14. More specifically, as shown in FIG. 1, a fluid pump 28 can be activated to pump a medical grade fluid from a fluid reservoir 30 and through the inflation tube 18 to inflate the balloon 14.

Figure 3:
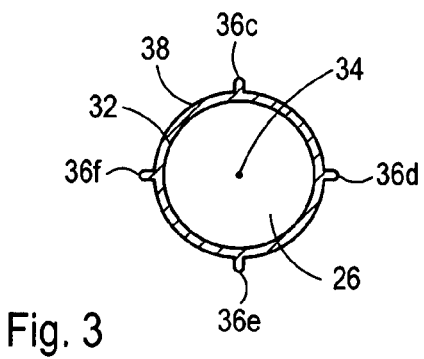
FIG. 3 is a cross-sectional view of the catheter shown in FIG. 2 as seen along line 3—3 in FIG. 2.

The structure of the flexible member 24 can perhaps best be appreciated with cross-reference to FIGS. 2 and 3. As seen there, the flexible member 24 includes a wall 32 that is substantially cylindrical shaped and defines a longitudinal axis 34. As further shown, a plurality of protuberances 36, of which exemplary protuberances 36a–f have been labeled, are formed on the outer surface 38 of the flexible member 24. Also shown, the wall 32 and protuberances 36 are formed together in a unitary, one-piece construction, and accordingly, are both made of the same material which is typically polyethylene terephthalate (PET). With this structural combination, the wall 32 seamlessly interconnects the protuberances 36 together. As further shown, each protuberance 36 is substantially cylindrical, pyramidal or hemispherical shaped and extends radially from the wall 32. For the embodiment shown, four longitudinally aligned rows of cleat-like protuberances 36 are uniformly distributed around the circumference of the cylindrical wall 32.

Figure 4:
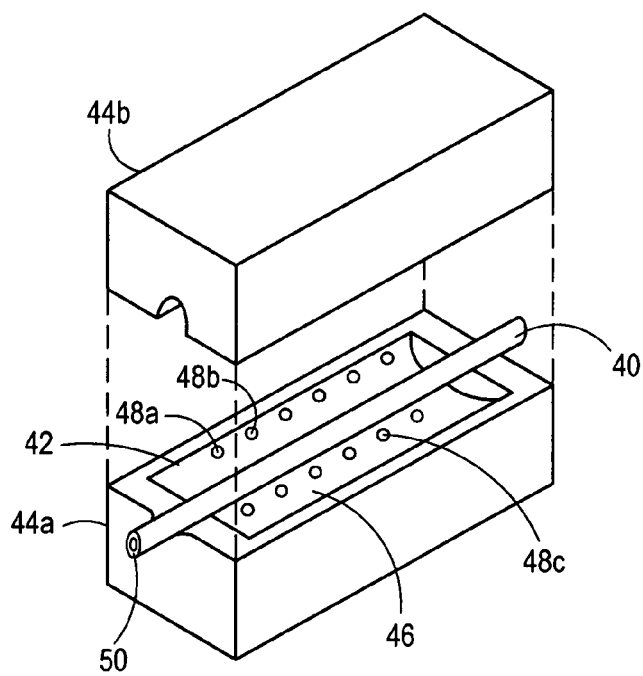
FIG. 4 is a simplified, perspective view of a blow-mold operation that can be used to manufacture the balloon shown in FIG. 2.

FIG. 4 illustrates one method for manufacturing the balloon 14 shown in FIG. 2. In this method, a tube 40 made of a polymeric material such as polyethylene terephthalate (PET) is heated to a working temperature and placed in the cavity 42 of a two-piece mold 44a,b. For this method, the mold 44 is formed with a substantially cylindrical-shaped mold surface 46 having a plurality of substantially cylindrical recesses 48, of which exemplary recesses 48a–c have been labeled. As shown, each recess 48 is cylindrical shaped to conform to the cylindrical shape of a protuberance 36 (See FIG. 2). With the tube 40 in the mold cavity 42 and the mold 44 closed, the lumen 50 of the tube 40 is pressurized to radially expand the tube 40 onto the mold surface 46. It is to be appreciated that portions of the tube 40 will flow into each recess 48. The result is a balloon 14 having protuberances 36 as shown in FIG. 2.

Figure 5:
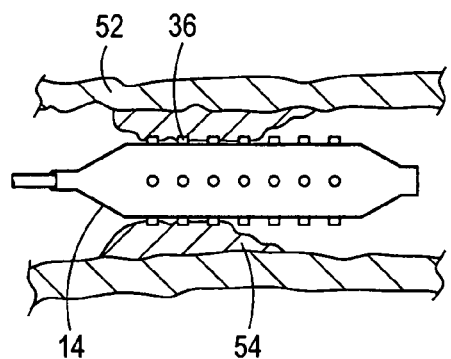
FIG. 5 is an enlarged view of the distal end of the catheter shown in FIG. 1 positioned at a treatment site and after the balloon has been inflated to embed the protuberances into a lesion to anchor the balloon at the treatment site.

A typical use of the catheter 12 can best be appreciated with cross-reference to FIGS. 1 and 5. In a typical use, the balloon 14 is deflated and the distal end of the catheter 12 is inserted into the vasculature of the patient 13 using a peripheral artery, such as the femoral artery, for access. Once in the vasculature, the distal end of the catheter 12 is advanced to a treatment site such as the treatment site shown in FIG. 5, which illustrates a coronary artery 52 that is constricted by a lesion 54. With the working section of the balloon 14 positioned adjacent to the lesion 54, the fluid pump 28 is activated to pass a fluid through the inflation tube 18 and into the balloon 14. As the balloon 14 expands, one or more of the protuberances 36 penetrate into and embed in the lesion 54, as shown. Once embedded, the protuberances 36 anchor the balloon 14, preventing longitudinal movement of the balloon 14 during further inflation of the balloon 14. Thus, the balloon 14 can be further inflated without longitudinal balloon movement to compact the lesion 54 and dilate artery 52. In addition to anchoring the balloon 14, the protuberances 36 can act as stress concentrators and cut initiators. For example, a plurality of pyramidal-shaped protuberances 36 can be used to create a pattern of indentations in the lesion 54.

Figure 6:
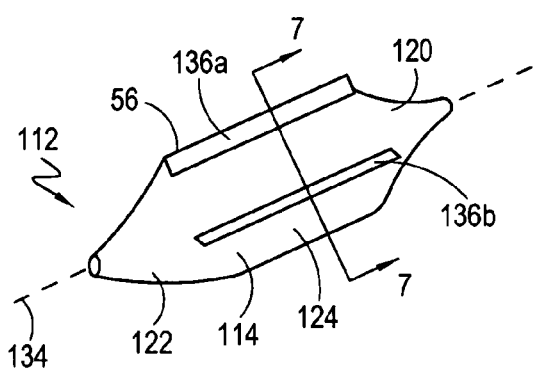
FIG. 6 is an enlarged, perspective view of the distal end of another embodiment of a catheter having a balloon and a system for anchoring the balloon at an internal treatment site.
Figure 7:
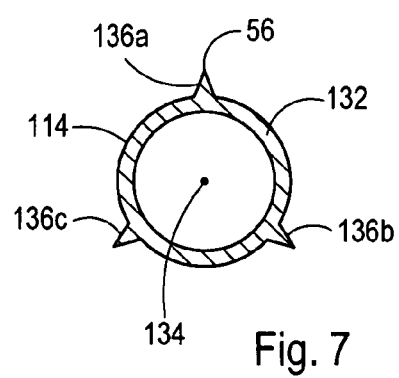
FIG. 7 is a cross-sectional view of the catheter shown in FIG. 6 as seen along line 7—7 in FIG. 6.

FIGS. 6 and 7 show the distal end of another embodiment of a catheter (designated 112) for anchoring a balloon 114 at a treatment site. In this embodiment, the catheter 112 includes three protuberances 136a–c that are formed as raised ridges with each ridge extending radially from the wall 132 of the flexible member 124 to a relatively sharp edge 56 that is aligned substantially parallel to the longitudinal axis 134. At a treatment site, the balloon 114 can be inflated to embed the protuberances 136a–c into a lesion or vessel wall to anchor the balloon 114 at the treatment site. With cross-reference to FIGS. 6 and 7, it can be seen that the wall 132 and protuberances 136 are formed together in a unitary, one-piece construction, and accordingly, are both made of the same material which is typically polyethylene terephthalate (PET). With this cooperation of structure, the wall 132 seamlessly interconnects the protuberances 136 together.

Figure 8:
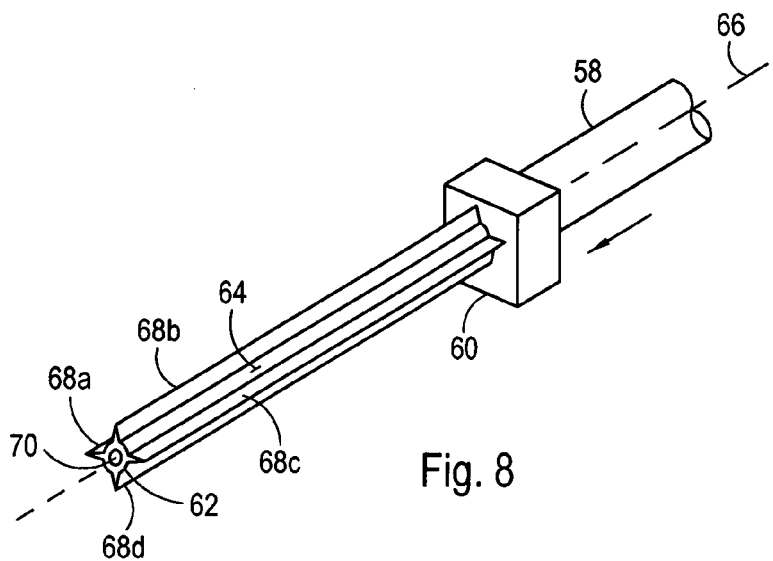
FIG. 8 is a simplified, perspective view of an extrusion operation for producing an extrusion that can be used to manufacture the balloon shown in FIG. 6.

FIG. 8 illustrates one method for manufacturing the balloon 114 shown in FIG. 6. In this method, a polymeric feed material 58 such as polyethylene terephthalate (PET) is heated to a working temperature and extruded through a die 60. As shown, the die 60 is configured to produce an extrusion 62 having a substantially cylindrically shaped wall 64 that is centered on an axis 66 and a plurality of longitudinally aligned ridges 68a–d that extend outwardly in radial directions from the wall 64. Next, the extrusion 62 is radially expanded to form the balloon 114 using, for example, a free-blow or blow-mold process. In the free-blow process, the ends of the extrusion 62 are held and the lumen 70 of the extrusion 62 is pressurized to radially expand the wall 64 (without a mold) and create the balloon 114. In the blow-mold process, a mold (not shown) that is similar to the mold 44 shown in FIG. 4 (but with modified recesses that are shaped to conform to the desired ridge shaped protuberances 136) is used. The extrusion 62 is expanded in the mold to create the balloon 114. Alternatively, the balloon 114 can be manufactured by expanding a tube (such as the tube 40 shown in FIG. 4) in a mold (not shown) having recesses that are shaped to conform to the desired ridge shaped protuberances 136.

In some cases, one or more portions of each protuberance 136 can be selectively removed (i.e., trimmed) to establish protuberances 136 having a desired shape and arrangement. For example, FIG. 6 shows a balloon 114 that results after portions of the protuberances 136 have been trimmed from the surfaces of the enclosures 120, 122. In an alternative method, selected portions of each ridge 68 (see FIG. 8) can be removed from the extrusion 62 prior to the blow-mold or free-blow process to thereby create a balloon 114 with protuberances 136 having a desired shape and arrangement.

Figure 9:
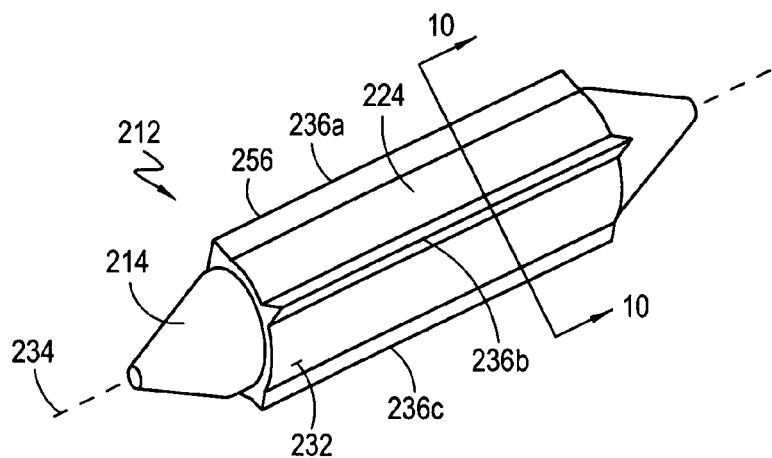
FIG. 9 is an enlarged, perspective view of the distal end of another embodiment of a catheter having a balloon and a system for anchoring the balloon at an internal treatment site.
Figure 10:
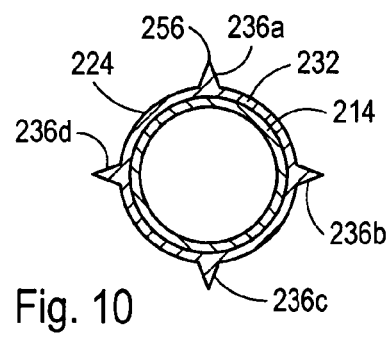
FIG. 10 is a cross-sectional view of the catheter shown in FIG. 9 as seen along line 10—10 in FIG. 9.

FIGS. 9 and 10 show the distal end of another embodiment of a catheter (designated 212) for anchoring a balloon 214 at a treatment site. In this embodiment, the catheter 212 includes a flexible member 224 that is formed as a jacket and bonded to the working portion of a dilatation balloon 214. As shown, the flexible member 224 includes a cylindrically shaped wall 232 and four protuberances 236a–d that are formed as raised ridges with each ridge extending radially from the wall 232 of the flexible member 224 to a relatively sharp edge 256 that is aligned substantially parallel to the longitudinal axis 234. At a treatment site, the balloon 214 can be inflated to embed one or more of the protuberances 236a–d into a lesion or vessel wall to anchor the balloon 214 at the treatment site. With cross-reference to FIGS. 9 and 10, it can be seen that the wall 232 and protuberances 236 are formed together in a unitary, one-piece construction, and accordingly, are both made of the same material which is typically polyethylene terephthalate (PET). With this cooperation of structure, the wall 232 seamlessly interconnects the protuberances 236 together.

Figure 11:
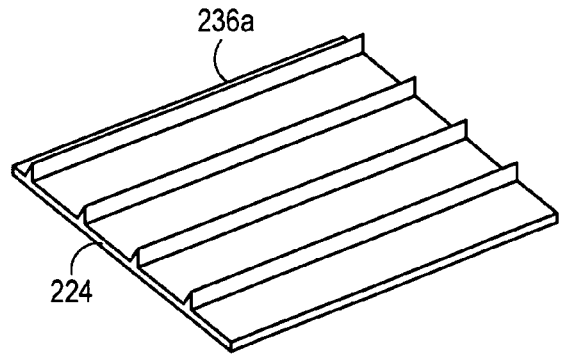
FIG. 11 is a simplified, perspective view of a flexible member for use in the manufacture of the balloon shown in FIG. 9.

FIG. 11 shows a one-piece, flexible member 224 that can be used to construct the catheter 212. For this manufacturing method, the flexible member 224 is typically made of a polymeric material and formed in either an extrusion or injection mold process. To manufacture the catheter 212, the flexible member 224 can be initially formed as a flexible sheet as shown in FIG. 11, having a plurality of protuberances 236. Once formed as a sheet, the flexible member 224 can be wrapped around the cylindrical portion of the balloon 214 and bonded to the balloon 214. For this manufacturing method, the flexible member 224 can be adhesively, thermally or ultrasonically bonded to the balloon 214. Alternatively, the flexible member 224 can be molded or extruded in the shape of a cylinder (i.e. molded or extruded in the configuration shown in FIG. 9) and then bonded to the balloon 214. Although raised ridges are shown in FIGS. 9–11, it is to be appreciated that a flexible member having protuberances in the shape of cleat-like cylinders (see FIG. 2) or some other shape and arrangement could be bonded to a balloon 214. Additionally, it is to be appreciated that although the embodiment shown in FIG. 9 includes a flexible member 224 that overlays the entire cylindrical portion of the balloon 214, one or more flexible members 224 to include longitudinally aligned strips and circumferential bands (not shown), with each strip or band having one or more protuberance 236, could be bonded to portions of the balloon 214.

While the particular system and method for anchoring a medical device to a lesion in a patient as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for anchoring a device to a lesion in the vasculature of a patient, which comprises:
   a flexible member defining an axis and having an inner surface and an outer surface, wherein said outer surface is formed with a plurality of solid integral protuberances seamlessly interconnected therewith to project radially outwardly therefrom;
   a balloon engaged with said inner surface of said flexible member for moving said member between a first configuration wherein said member is collapsed onto the axis and a second configuration wherein said member is made substantially rigid; and
   a longitudinally oriented cutting initiator formed on each said protuberance for penetrating said protuberances into the lesion and for anchoring the device to the lesion.

2. A system as recited in claim 1 wherein said member and said protuberances are made of a same selected material.

3. A system as recited in claim 1 wherein said inner surface of said member is bonded to said balloon for movement from the first configuration to the second configuration in response to an inflation of said balloon and for movement from the second configuration to the first configuration in response to a deflation of said balloon.

4. A system as recited in claim 3 wherein said member is ultrasonically bonded to said balloon.

5. A system as recited in claim 1 further comprising a fluid pump for inflating said balloon.

6. A system as recited in claim 1 wherein said protuberances are a plurality of raised ridges with said ridges oriented substantially parallel to the axis.

7. A system as recited in claim 6 wherein each said ridge extends radially to an edge that is aligned substantially parallel to the axis.

8. A system for anchoring a device to a lesion in the vasculature of a patient, which comprises:
   a flexible member defining an axis and having an inner surface and an outer surface, with said member having a plurality of solid protuberances projecting radially outward from said outer surface, wherein said member and said protuberances are seamlessly interconnected and are made of a same selected material;
   a balloon engaged with said inner surface of said flexible member for moving said member between a first configuration, wherein said member is collapsed onto the axis, and a second configuration, wherein said member is substantially rigid and is distanced from the axis;
   a longitudinally oriented cutting initiator formed on each said protuberance for penetrating said protuberances into the lesion; and
   a means for projecting said protuberances radially away from the axis to penetrate said protuberances into the lesion and anchor the device to the lesion.

9. A system as recited in claim 8 wherein the selected material is polyethylene terephthalate (PET).

10. A system as recited in claim 8 wherein said protuberances are a plurality of raised ridges with each said ridge extending to an edge that is aligned substantially parallel to the axis.

11. A system for anchoring a device to a lesion in the vasculature of a patient, which comprises:
    a tubular-shaped flexible member having a first end and a second end and defining an axis, said member having an inner surface and an outer surface, wherein said outer surface is formed with a plurality of solid integral protuberances longitudinally oriented and seamlessly interconnected therewith to project radially outwardly therefrom;
    a balloon engaged with said inner surface of said flexible member for moving said member between a first configuration wherein said member is collapsed onto the axis and a second configuration wherein said member is made substantially rigid; and
    a means for embedding said protuberances into the lesion and for anchoring the device to the lesion.

12. A system as recited in claim 11 wherein said means for moving said member between the first configuration and the second configuration comprises a fluid pump.

13. A system for anchoring a device to a lesion in the vasculature of a patient, which comprises:
    a flexible member defining an axis and having an inner surface and an outer surface, wherein said outer surface is formed with a plurality of solid integral protuberances longitudinally oriented and seamlessly interconnected therewith to project radially outwardly therefrom, said protuberances being a plurality of raised ridges with said ridges oriented substantially parallel to the axis;
    a balloon engaged with said inner surface of said flexible member for moving said member between a first configuration wherein said member is collapsed onto the axis and a second configuration wherein said member is made substantially rigid; and
    a means for embedding said protuberances into the lesion and for anchoring the device to the lesion.

14. A system as recited in claim 13 wherein each said ridge extends radially to an edge that is aligned substantially parallel to the axis.

15. A system as recited in claim 13 wherein said inner surface of said member is bonded to said balloon for movement from the first configuration to the second configuration in response to an inflation of said balloon and for movement from the second configuration to the first configuration in response to a deflation of said balloon.

16. A system as recited in claim 15 wherein said member is ultrasonically bonded to said balloon.

* * * * *